United States Patent
Ringermacher et al.

(10) Patent No.: US 8,393,784 B2
(45) Date of Patent: Mar. 12, 2013

(54) CHARACTERIZATION OF FLAWS IN COMPOSITES IDENTIFIED BY THERMOGRAPHY

(75) Inventors: Harry Israel Ringermacher, Delanson, NY (US); Donald Robert Howard, Troy, NY (US); Bryon Edward Knight, Charlton, NY (US); William George Patterson, Wilmington, DE (US); Thomas Edward Bantel, Cincinnati, OH (US)

(73) Assignee: General Electric Company, Schenectady, NY (US)

( * ) Notice: Subject to any disclaimer, the term of this patent is extended or adjusted under 35 U.S.C. 154(b) by 1141 days.

(21) Appl. No.: 12/059,172

(22) Filed: Mar. 31, 2008

(65) Prior Publication Data
US 2009/0245321 A1    Oct. 1, 2009

(51) Int. Cl.
G01N 25/72    (2006.01)
G01N 25/58    (2006.01)
G01J 5/00    (2006.01)

(52) U.S. Cl. ............... 374/5; 374/45; 374/57; 374/121; 250/338.1

(58) Field of Classification Search ............... 374/1, 4, 374/5, 7, 29, 30, 43–45, 57, 100–104, 111, 374/112, 115, 120, 121, 124, 129, 134, 137, 374/141, 166, 167, 170; 250/338.1, 341.6, 250/330, 332; 324/238
See application file for complete search history.

(56) References Cited

U.S. PATENT DOCUMENTS

| | | | | |
|---|---|---|---|---|
| 4,446,354 | A | * | 5/1984 | Kearney .................. 219/130.01 |
| 4,724,481 | A | * | 2/1988 | Nishioka ....................... 348/133 |
| 5,444,241 | A | * | 8/1995 | Del Grande et al. .......... 250/253 |
| 5,582,485 | A | * | 12/1996 | Lesniak ........................... 374/5 |

(Continued)

FOREIGN PATENT DOCUMENTS

DE    10053112 A1 *    5/2002
EP       89760 A2 *    9/1983

(Continued)

OTHER PUBLICATIONS

"Discriminating Porosity in Composites Using Thermal Depth Imaging", H.I. Ringermacher, D.R. Howard, and R.S. Gilmore, General Electric Research and Development Center.

(Continued)

*Primary Examiner* — Gail Verbitsky
(74) *Attorney, Agent, or Firm* — General Electric Company; Sushupta T. Sudarshan; David J. Clement

(57) ABSTRACT

A method for identifying types of flaws in a composite object includes: a) rapidly heating the surface of the object; b) recording pixel intensities in a sequence of IR images; c) determining temperature-versus-time data for each of the pixels from the IR images; and d) determining what type of flaw if any corresponds to each of the pixels using the temperature-versus-time data determined in step (c). A contrast curve derived from the temperature-versus-time data may be used in determining what type of flaws if any corresponds to each of the pixels. The contrast curve may be determined by subtracting a synthetic reference curve from a temperature time curve from the temperature-versus-time data. The types of flaws may be determined from size and/or shapes of peaks in the contrast curves. Some flaws are delaminations, layers of porosity, and uniformly distributed porosity.

14 Claims, 6 Drawing Sheets

U.S. PATENT DOCUMENTS

| | | | | |
|---|---|---|---|---|
| 5,709,469 | A * | 1/1998 | White et al. | 374/5 |
| 5,711,603 | A | 1/1998 | Ringermacher et al. | |
| 5,818,951 | A * | 10/1998 | Schivley | 382/100 |
| 5,828,448 | A * | 10/1998 | Jakobsen et al. | 356/237.1 |
| 6,000,844 | A * | 12/1999 | Cramer et al. | 374/5 |
| 6,172,502 | B1 * | 1/2001 | Groen et al. | 324/307 |
| 6,346,704 | B2 | 2/2002 | Kenway | |
| 6,367,968 | B1 | 4/2002 | Ringermacher et al. | |
| 6,367,969 | B1 * | 4/2002 | Ringermacher et al. | 374/7 |
| 6,394,646 | B1 * | 5/2002 | Ringermacher et al. | 374/7 |
| 6,516,084 | B2 * | 2/2003 | Shepard | 382/141 |
| 6,517,238 | B2 | 2/2003 | Sun et al. | |
| 6,585,146 | B2 * | 7/2003 | Shepard | 228/104 |
| 6,595,684 | B1 * | 7/2003 | Casagrande et al. | 374/5 |
| 6,690,016 | B1 * | 2/2004 | Watkins et al. | 250/341.7 |
| 6,698,288 | B2 | 3/2004 | Shirzad et al. | |
| 6,751,342 | B2 * | 6/2004 | Shepard | 382/141 |
| 6,840,666 | B2 * | 1/2005 | Enachescu et al. | 374/5 |
| 6,874,932 | B2 * | 4/2005 | Devitt et al. | 374/5 |
| 7,064,331 | B2 * | 6/2006 | Rothenfusser et al. | 250/341.6 |
| 7,082,833 | B2 * | 8/2006 | Heyman et al. | 73/598 |
| 7,220,966 | B2 * | 5/2007 | Saito et al. | 250/341.6 |
| 7,245,093 | B2 * | 7/2007 | Engel et al. | 318/135 |
| 7,516,663 | B2 * | 4/2009 | Ringermacher et al. | 73/601 |
| 7,549,789 | B2 * | 6/2009 | Tralshawala et al. | 374/43 |
| 7,554,086 | B2 * | 6/2009 | Shepard et al. | 250/341.1 |
| 7,591,583 | B2 * | 9/2009 | Foes et al. | 374/5 |
| 7,712,502 | B2 * | 5/2010 | Engelbart et al. | 156/351 |
| 2002/0027941 | A1 * | 3/2002 | Schlagheck et al. | 374/5 |
| 2002/0172410 | A1 * | 11/2002 | Shepard | 382/141 |
| 2005/0008215 | A1 * | 1/2005 | Shepard | 382/141 |
| 2005/0098728 | A1 * | 5/2005 | Alfano et al. | 250/341.8 |
| 2005/0186327 | A1 * | 8/2005 | Saito et al. | 427/8 |
| 2007/0288177 | A1 | 12/2007 | Rothenfusser et al. | |
| 2008/0008968 | A1 * | 1/2008 | Zombo | 430/311 |
| 2008/0022775 | A1 * | 1/2008 | Sathish et al. | 73/606 |
| 2008/0107147 | A1 * | 5/2008 | Kollgaard et al. | 374/5 |
| 2008/0317334 | A1 * | 12/2008 | Hausler | 382/154 |
| 2009/0000382 | A1 * | 1/2009 | Sathish et al. | 73/606 |
| 2009/0297017 | A1 * | 12/2009 | Hudgings et al. | 382/141 |
| 2010/0033565 | A1 * | 2/2010 | Benzerrouk et al. | 348/125 |

FOREIGN PATENT DOCUMENTS

| | | | |
|---|---|---|---|
| GB | 2269454 A * | 2/1994 | |
| GB | 2275773 | 7/1994 | |
| JP | 2000131220 A * | 5/2000 | |

OTHER PUBLICATIONS

"Defects Detection and Characterization Using Leaky Lamb Wave (LLW) Dispersion Data" by Yoseph Bar-Cohen and Ajit Mal and Zensheu Chang, ASNT '98 Spring Conference, Joint with 9th Asia-Pacific Conference on NDT, and 7th Annual Research Symposium, Aging Aircraft Track, Anaheim, CA, Mar. 24-26, 1998.

"Techniques for the Nondestructive Evaluation of Polymer Matrix Composites" by George A. Matzkanin and H. Thomas Yolken, AMMTIAC, Rome, NY, The AMMTIAC Quarterly, vol. 2, No. 4 http://ammtiac.alionscience.com/quarterly.

"Composite Material Defects Characterization Using Leaky Lamb Wave Dispersion Data", by Yoseph Bar-Cohen, Ajit Mal and Zensheu Change, SPIE's NDE Techniques for Aging Infrastructure & Manufacturing, Conference NDE of Materials and Composites II, Mar. 31-Apr. 2, 1998, San Antonio, SPIE Copyright 1998.

"Characterization of Defects in Composite Material Using Rapidly Acquired Leaky Lamb Wave Dispersion Data", by Yoseph Bar Cohen, Zensheu Chang and Ajit Mal, NDT net—Sep. 1998, vol. 3 No. 9.

"Nondestructive Inspection of Composite Structures: Methods and Practice", by David K. Hsu, Center for Nondestructive Evaluation, Iowa State University, 17th World Conference on Nondestructive Testing, Oct. 25-28, 2008, Shanghaim China.

XP-002523281, "NDE of composite materials by Thermal method and Shearography", P.G. Bison, C. Bressan, G. Cavaccini, A. Ciliberto, E. Grinzato, CNR-ITEF, Corso Stati Uniti, 4, 35127—Padova, Italy, 10 pages, Oct. 2008.

"Defect detection in aircraft composites by using a neural approach in the analysis of thermographic images", Elsevier, Science Direct, NDT&E International, T. D'Orazio, C. Guaragnella, M. Leo, P. Spagnolo, CNR-ISSIA Via Amendola 122/D-I, 70126 Bari, Italy, DEE Politecnico di Bari Via Orabona 70126 Bari, Italy, Received Nov. 2, 2004; revised Mar. 16, 2005; accepted Apr. 10, 2005; Available online Jun. 13, 2005, 10 pages.

Patent Cooperation Treaty, PCT International Search Report, From the International Searching Authority, Received May 11, 2009 Global Patent Operation, 3 pages.

XP-000863003, "Thermographic Imaging for High-Temperature Composite Materials—A Defect Detection Study", D.J. Roth, J.R. Bodis, C. Bishop, 24 pages, 1997.

Patent Cooperation Treaty, PCT International Search Report, (PCT Article 18 and Rules 43 and 44), 4 pages, Feb. 2009.

* cited by examiner

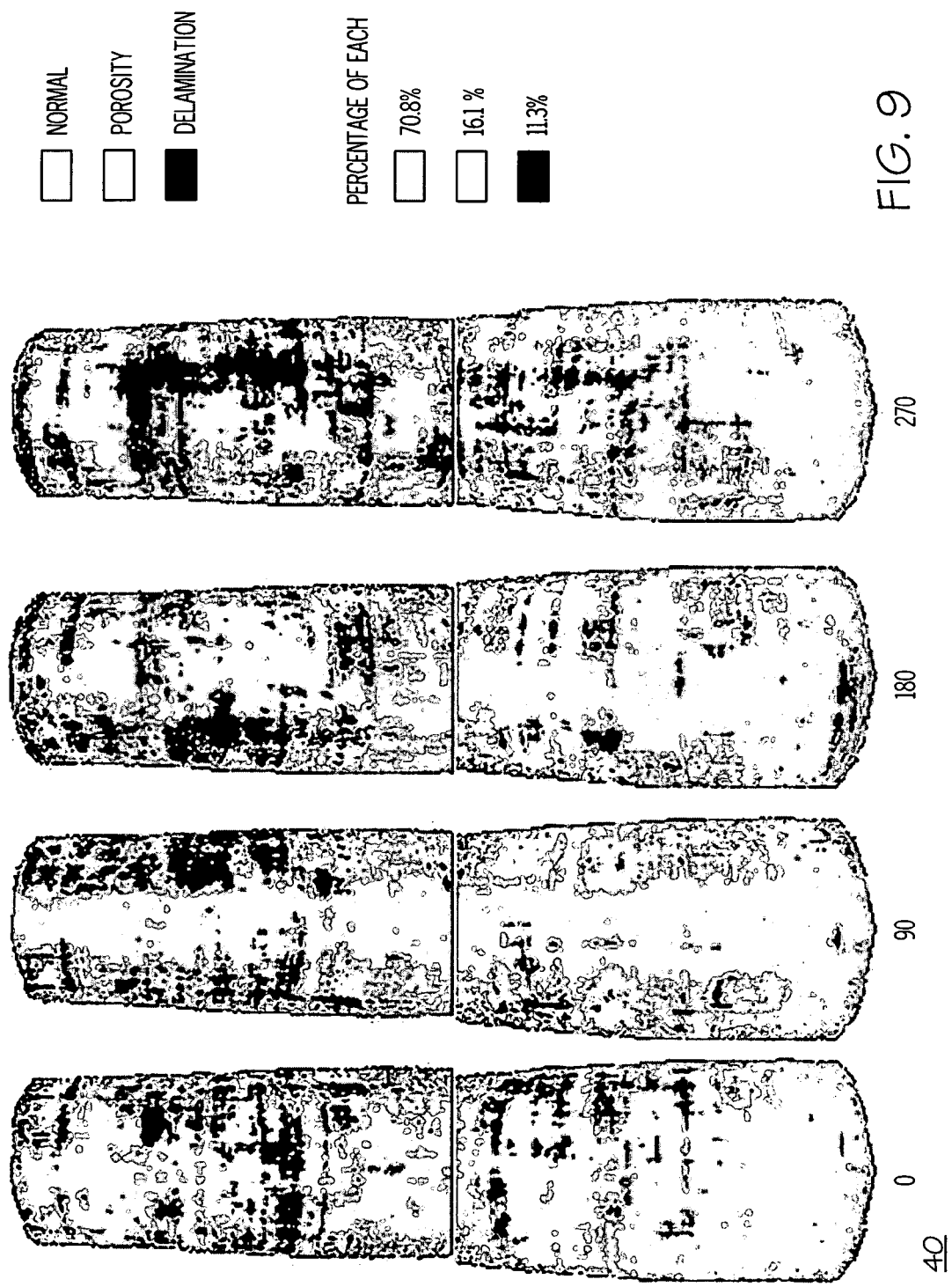

CHARACTERIZATION OF FLAWS IN COMPOSITES IDENTIFIED BY THERMOGRAPHY

BACKGROUND OF THE INVENTION

1. Field of the Invention

This invention relates generally to thermography and, more particularly, to using thermography to identify material characteristic flaws in articles made of composite materials.

2. Description of Related Art

Thermography has been used to locate material characteristic flaws in articles including articles made of composite materials. Composite materials include both polymers and ceramics. Thermography has been used to show flaws appearing in composites via their characteristic time-temperature contrast signatures obtained with infrared thermography. Thermography has been used to locate the flaws that alter the flow of heat but did not identify what types of material characteristic flaws were found. Material characteristic flaws in composites typically include porosity and delaminations as contrasted to size, location, and depth of flaws.

Thermography is a non-destructive evaluation (NDE) technique in which heat is applied to an object and a resulting temperature distribution on a surface of the object is measured over time with an infrared camera. Information about flaws in the object is obtained from the recorded infrared time sequence. Images are digitized into picture elements, or pixels, each representing a small unit area on the object's surface. A temperature/time signal is processed and evaluated per pixel and in patterns of pixels.

One known contemporary application of transient thermography, that provides the ability to determine the size and "relative" location (depth) of flaws within solid non-metal composites, is disclosed in U.S. Pat. No. 5,711,603 to Ringermacher et al., entitled "Nondestructive Testing: Transient Depth Thermography"; and is incorporated herein by reference. The method disclosed therein involves heating the surface of an object of interest and recording the temperature changes over time of very small regions or "resolution elements" on the surface of the object. The method provides for determining a size and a value indicative of a "relative" depth of a flaw (i.e., relative to other flaws within the object) based upon a careful analysis of the temperature changes occurring at each resolution element or pixel over the surface of the object.

U.S. Pat. No. 6,367,968, entitled "Thermal Resonance Imaging Method" to Ringermacher et al., discloses an infrared (IR) transient thermography system for producing a sequence of image frames acquired from an IR sensitive focal-plane array camera. U.S. Pat. No. 6,367,969, entitled "Synthetic Reference Thermal Imaging Method" to Ringermacher et al., discloses an infrared (IR) transient thermography system for producing a sequence of image frames acquired from an IR sensitive focal-plane array camera. Each frame is made up of an array of pixels and has assigned a frame-number that corresponds to elapsed time. Temperature-versus-time (T-t) data corresponding to each pixel is developed from stacks of sequential image-frames. Also disclosed is a method of analyzing the stacks of thermal data image frames to determine the thickness of an object and produce a color-keyed or gray-scale coded thickness map. U.S. Pat. No. 6,367,969, entitled "Synthetic Reference Thermal Imaging Method" to Ringermacher et al., discloses an infrared (IR) transient thermography system in which a sequence of image frames is acquired from an IR sensitive focal-plane array camera. Each sequentially acquired image frame is made up of an array of pixels and has assigned a frame number that corresponds to elapsed time. A method of analyzing thermal imaging data-frames is presented wherein a synthetically generated temperature-time reference curve is used to determine pixel contrast-versus-time data. U.S. Pat. No. 6,367,968 and U.S. Pat. No. 6,367,969 are both assigned to the General Electric Company, the assignee of this patent, and are incorporated herein by reference.

A surface of an object is heated to a particular temperature in a sufficiently short period. Depending on the thickness and material characteristics of the object under test, a quartz lamp or a high intensity flash-lamp is conventionally used to generate a heat pulse of the proper magnitude and duration. Any means capable of quickly heating the surface to a temperature sufficient to permit thermographic monitoring—such as, for example, pulsed laser light may be used. Once the surface of the object is heated, a graphic record of thermal changes over the surface is acquired and analyzed as the object cools down.

An infrared (IR) video camera is used to record and store successive thermal images (frames) of an object surface after heating it. Each video image is composed of a fixed number of pixels. In this context, a pixel is a small picture element in an image array or frame that corresponds to a rectangular area, called a "resolution element", on the surface of the object being imaged. Since, the temperature at each resolution element is directly related to the intensity of the corresponding pixel, temperature changes at each resolution element on the object surface can be analyzed in terms of changes in pixel contrast. The stored IR video images are used to determine the contrast of each pixel in an image frame by subtracting the mean pixel intensity for a particular image frame, representing a known point in time, from the individual pixel intensity at that same point in time.

Several systems and methods, including ones in the patents cited above, disclose how to use this data to identify and determine depths of flaws have been disclosed. What they do not disclose is how to characterize or identify what material characteristic type of flaws were found such as delaminations and porosity. It is desirable to have a nondestructive testing method to find flaws in composite articles and identify what type of material characteristic flaws were found. It is particularly desirable to have a nondestructive testing method to find material characteristic flaws and identify or discriminate between porosity and delaminations.

BRIEF SUMMARY OF THE INVENTION

A method for identifying material characteristic types of flaws in a composite object includes the following steps: a) rapidly heating the surface of the object; b) recording pixel intensities in a sequence of IR images, each image sequentially related to time elapsed since heating the surface in step (a); c) determining temperature-versus-time data for each of the pixels from the IR images; and d) determining what material characteristic type of flaw if any corresponds to each of the pixels using the temperature-versus-time data determined in step (c).

A contrast curve for each of the pixels may be determined from the temperature-versus-time data for each of the pixels and the contrast curve used for determining what material characteristic type of flaws if any corresponds to each of the pixels. The contrast curve may be derived by determining a synthetic reference curve from synthetic thermal reference temperature-versus-time data and subtracting the synthetic reference curve from a temperature time curve determined from the temperature-versus-time data from step (c).

The flaws may include delaminations characterized by the contrast curves having large broad peaks, distinct layers of porosity characterized by the contrast curves having leading peaks followed by shallow troughs in the contrast curves, distinct extended layers of porosity characterized by the contrast curves having leading peaks followed by plateaus in the contrast curves, and uniformly distributed porosity characterized by a uniformly distributed porosity contrast curve substantially shifted from a no defect contrast curve. The uniformly distributed porosity contrast curve and the no defect contrast curve each has an inflection point.

One embodiment of the method further includes displaying areas of the object corresponding to the pixels characterized by the different types of flaws and no flaws. Another more particular embodiment of the method further includes displaying the areas of the object in different colors corresponding to the pixels characterized by the types of flaws and no flaws.

BRIEF DESCRIPTION OF THE DRAWINGS

The foregoing aspects and other features of the invention are explained in the following description, taken in connection with the accompanying drawings where:

FIG. 9 is a black and white illustration of a color picture produced using the thermography system and method illustrated in FIG. 1 and showing a composite gas turbine engine combustor liner having areas of no flaws, porosity flaws, and delamination flaws.

DETAILED DESCRIPTION OF THE INVENTION

Figure 1:
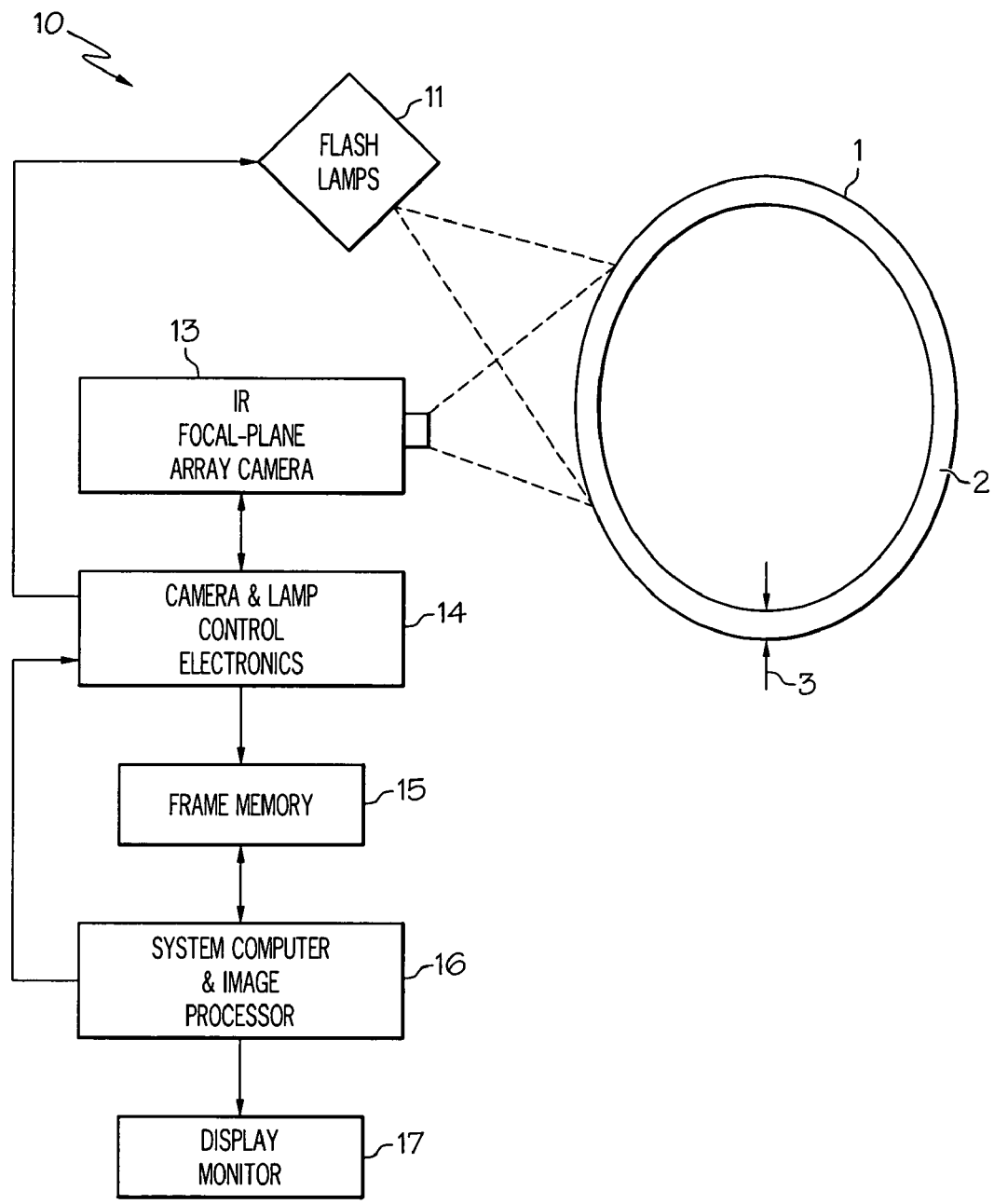
FIG. 1 is a schematic diagram illustrating an exemplary infrared transient thermography system and method for determining and characterizing flaws in articles made of composite materials.

Illustrated in FIG. 1 is an IR transient thermography system 10 for identifying and characterizing flaws, e.g. delaminations and porosity, in a composite object 1, e.g. a composite gas turbine engine combustor liner having a composite wall 2 of thickness 3. A flash-lamp heat-pulse source 11 is used to rapidly heat the surface of the object being analyzed. One suitable arrangement for flash-lamp heat-pulse source 11 would be, for example, a set of four or eight high-speed, high output power photographic flash-lamps, each capable of about 4.8 Kilo-joules output and having individual power supplies (such as, for example, flash-lamps manufactured by Speedotron, Corp. in Chicago, Ill.).

Figure 2:
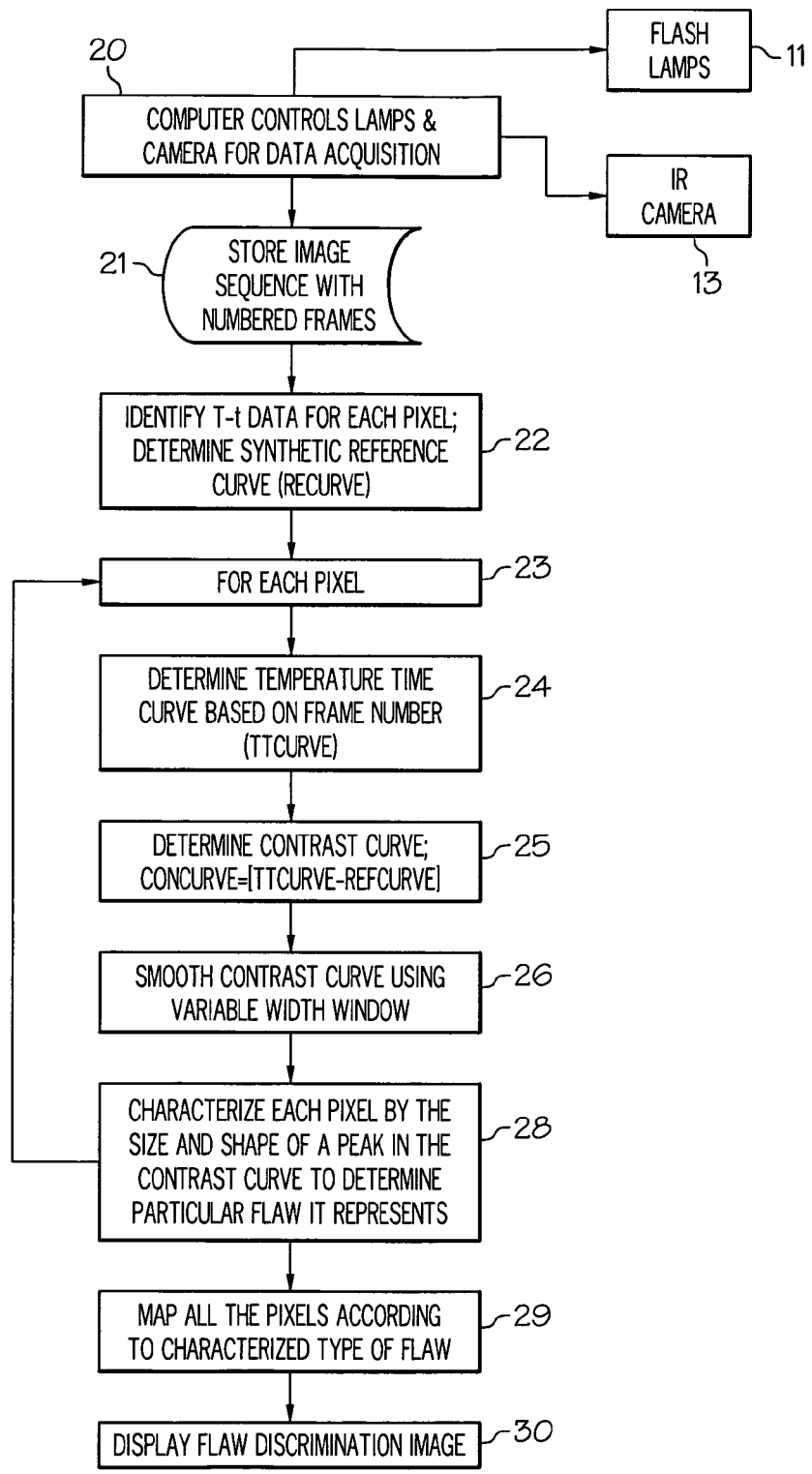
FIG. 2 is a flow chart illustrating the method of determining and characterizing flaws as performed by the system of FIG. 1.

An exemplary infrared transient thermography method for determining and characterizing flaws in articles made of composite materials is outlined in blocks of a flow chart illustrated in FIG. 2 and using the system illustrated in FIG. 1. Surface temperature measurements of heat-pulse illuminated object 1 are acquired in block 20 of the flow chart in FIG. 2 after the object has been heated and when it begins to cool down. The surface temperature measurements are made using a infrared (IR) sensitive imaging system including an IR sensitive focal-plane array camera 13 (e.g., a Phoenix camera may be available from FLIR CORP.), control electronics 14, frame data memory 15, control computer and image processor 16 and display monitor 17. Acquisition of thermal data is initiated right after the flash-lamp firing either by optical triggering or by other suitable means. Flash-lamp firing is controlled via conventional flash-lamp electronics 14 managed by conventional video frame acquisition software running on system computer (such as provided by the Image Desk™ frame acquisition system from FLIR Corp.) or other conventional frame acquisition and flash-lamp control software, for example, such as commercially available from Thermal Wave Imaging Inc. in Lathrup Village, Mich.).

The system control computer and image processor 16 is a specially programmed general purpose digital computer that is capable of peripheral equipment control and communication functions in addition to digital image processing and display in accordance with the method of the present invention. The system computer controls camera and lamp electronics 14 and frame data memory 15 to acquire a predetermined number of successive thermal image frames of the object surface which are stored in the memory 15 for future analysis.

Before beginning the thermal imaging process, IR camera 13 is first calibrated using a "full-field" dual-image calibration technique as now described. This preferred technique employs two "black-body" (BB) image calibration references: a BB "cold" source using a room-temperature flat-black plate and a BB "hot" source using a heated flat-black plate. For example, for acquiring the BB "cold" source calibration image, a heavy copper-based plate coated with carbon-black is placed directly in front of the lens. For acquiring the BB "hot" source calibration image, the camera lens is placed into the same flat-black painted box unit after heating the flat-black plate, nominally to about 10 degrees C. above ambient, such that the camera images the heated plate over its full field. The above described dual-image calibration technique is just one type, any calibration technique that results in producing maximum uniformity of the image field, that is important for high contrast imaging and obtaining good thermal accuracy, can be used.

Referring to FIG. 2, the flow chart illustrates exemplary processing steps for conducting transient IR thermography using synthetic-reference thermal imaging techniques. These steps are illustrated as being implemented by a computer (FIG. 1) using known conventional programming techniques. At block 20, a region of interest on the object 1 is identified (i.e., the IR camera is focused to capture the region of interest) and the system operator selects or inputs information concerning relevant parameters for examining the object such as, for example, a thermal diffusivity coefficient for the material.

Figure 3:
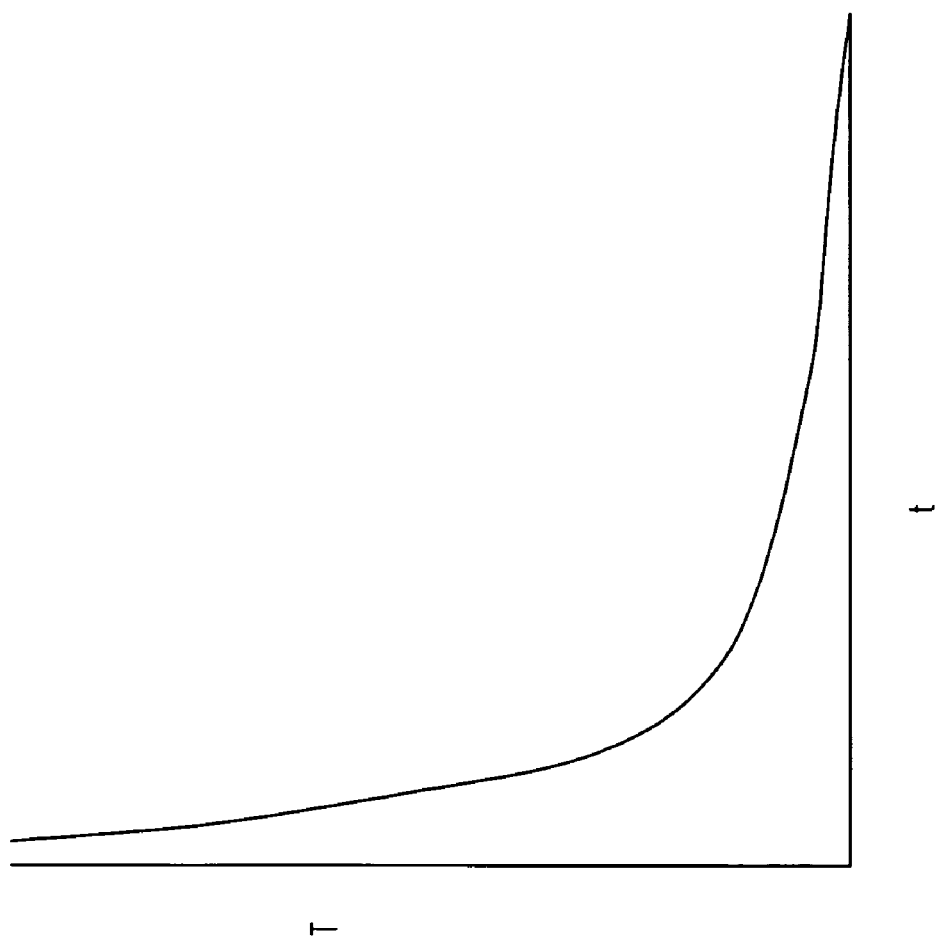
FIG. 3 is a graph of an exemplary temperature versus time curve for a pixel.

Next, as indicated at block 20 in FIG. 2, the system control computer instructs the flash-lamp electronics to fire the flash-lamps and initiate image frame data acquisition from the focal plane array IR camera 13. Data acquisition proceeds over a predetermined number of sequential image frames and then, as indicated at block 21, the image sequence is stored in the frame memory 15 after identifying each acquired image frame with a sequential frame number Z. Each image frame acquired during the imaging process consists of N×N pixels. Each pixel corresponds to a resolution element on the object surface and N is typically either 128 or 256 depending on the resolution and accuracy desired. Each pixel occupies about two bytes of storage memory and may be represented, for example, by a 12-bit or larger binary number. The stored image frames are sequentially identified with increasing frame number values which together serve to provide a historical record of the temperature vs. time (T-t) as illustrated in FIG. 3 for a front surface of the object 1 for a predetermined period of time after being struck by the heat impulse imparted by flash-lamps.

During evaluation of a composite object, after control computer triggers the firing of flash-lamp(s), image data frames are acquired from camera 13 and the IR intensity at each resolution element on the image is digitally saved in frame data memory 15 or may be recorded and stored in a frame data recorder. As indicated in block 22, the exemplary method disclosed herein determines a synthetic reference curve (REFCURVE) from synthetic thermal reference T-t data. U.S. Pat. No. 6,367,969 discloses a method suitable to determine the synthetic thermal reference T-t data and reference curve (REFCURVE). Determining the synthetic thermal reference T-t data includes identifying a time and frame number of the initial IR "flash" heating and a first unsaturated data frame. A "synthetic" half-space thermal decay T-t reference data curve is generated based upon an initial surface temperature parameter and a flash duration to be used in determining the synthetic thermal reference T-t data.

As indicated in blocks 23 and 24, data acquisition continues for each pixel over a predetermined number of sequential image frames that are sufficient to acquire a meaningful T-t (temperature vs. time) history over a duration of at least one estimated "characteristic time period" for the material of the object. A temperature time curve (T-t CURVE) is determined based on the images that represent intensity-versus-time data of each pixel derived from the measured IR intensity. The total number of image frames acquired may vary depending on the accuracy and image resolution desired and can be as high as 1200 frames per second of data acquisition. Frame data may be stored in memory or a recorder may be a conventional digital memory internal to the processor 16 or any suitable video frame data storage device accessible by processor 16. Each successive thermal image frame acquired is assigned an increasing frame number, Z, corresponding to the passage of real time. The resulting data frame "stack" is then analyzed taking a one-dimensional heat flow analysis approach, as outlined above.

Contrast-versus-time data for each pixel is calculated using the intensity-versus-time data and the synthetic thermal reference T-t data. Contrast curves C (see FIGS. 4, 5, and 7) are determined by subtracting the synthetic reference curve (REFCURVE) from the temperature time curve (TTCURVE) as denoted in block 25. As indicated at block 26, contrast curves C are mathematically smoothed such as by Gaussian function temporal smoothing.

The acquisition of surface temperature data is initiated by firing the flash-lamps to illuminate the surface of the object. A predetermined number of image frames are then recorded over a period of time after the flash-lamps are fired and the recorded images used to develop the temperature-time (T-t) history for every elemental region or "resolution element" over the region of interest on the object surface as indicated in block 24. Each recorded image frame includes a predetermined N×N array of image pixels whose intensity correlate to the surface temperature of the object at the time the frame data was acquired. Each pixel has a location designation within the image frame that corresponds to a particular resolution element.

Figure 5:
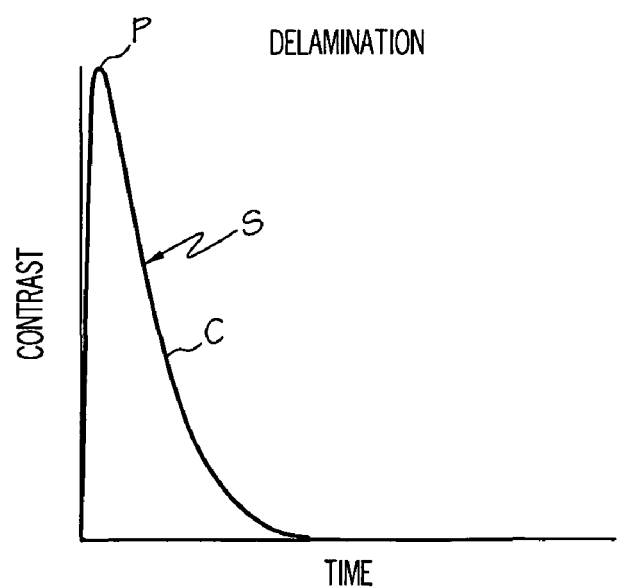
FIG. 5 is a graph of an exemplary contrast curve for a pixel in an area of the composite article having a delamination flaw.
Figure 6:
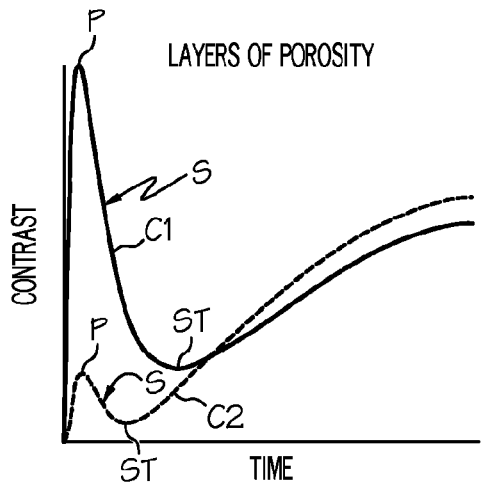
FIG. 6 is a graph of an exemplary contrast curve for a pixel in an area of the composite article having distinct layers of porosity flaw.
Figure 7:
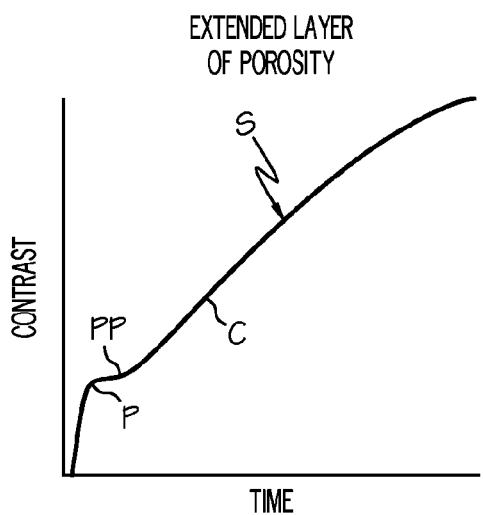
FIG. 7 is a graph of an exemplary contrast curve for a pixel in an area of the composite article having a distinct extended layer of porosity flaw.

The heat flow analysis of the T-t history for each pixel in the acquired image frames is also used to determine the thickness of the flaw at each resolution element location. As indicated in block 25 recorded intensity-versus-time history of the pixel is used to compute contrast-versus-time data for the pixel as illustrated by exemplary contrast curves C illustrated in FIG. 4-8. A particular flaw is characterized by the size and the shape of the peak in the contrast curve over a characteristic time period TC as indicated in block 28. Porosity has a characteristic leading peak LP, small or large, followed by a shallow trough ST such as is illustrated in FIG. 6 or a plateau PP such as is illustrated in FIG. 7 and a depth indication. Delaminations have large, broad peaks with depth indications much like ideal plates. Porosity can occur in discrete layers or in thicker zones also referred to as uniformly distributed porosity, each with characteristic signature.

The exemplary method disclosed herein subtracts synthetic thermal reference T-t data from the recorded intensity-versus-time data of the pixel to calculate contrast-versus-time data represented as the contrast curves as illustrated herein. U.S. Pat. No. 6,367,968 discloses a method suitable to calculate the synthetic thermal reference T-t data. Using the synthetic thermal reference, the contrast-versus-time curve or contrast curve is determined for each pixel corresponding to each resolution element of the object's surface. Next, Gaussian temporal smoothing of the pixel contrast curve data is employed to improve the signal-to-noise ratio of the measurements. A shape S and a height H of a peak P of the contrast curve, as illustrated in FIGS. 5 and 6, if there is one is then computed or otherwise determined to identify or characterize the material characteristic type of flaw or lack thereof for the pixel in the data. The various flaws are discriminated with the above method and then mapped against locations of the pixels of the object as indicated in block 29.

The "synthetic" or computed thermal reference may be used instead of a "real" reference such as a slab standard or a suitable region on the examined object. An exemplary method for calculating and determining synthetic thermal reference T-t data is disclosed in U.S. Pat. No. 6,367,969 which is incorporated herein by reference. The formula for calculating the synthetic temperature $T_s$, as a function of time t is $T_s(t) = A[t^{1/2} - (t-TAU)^{1/2}]$. A is a calibration constant and TAU is the fixed length in time of the flash pulse. The reference temperature-time data provided by this equation describes a "synthetic" half-space thermal decay based on an initial temperature, A, at a particular location on the surface of the object. The "synthetic" thermal reference data as obtained from this equation is first computed for each (x,y) pixel location of the imaged object and then used to determine contrast as a function of time for each pixel.

Figure 4:
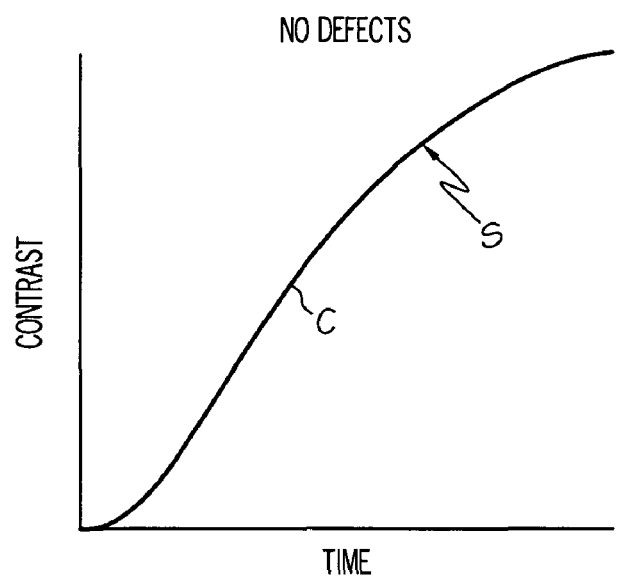
FIG. 4 is a graph of an exemplary contrast curve for a pixel in an area of the composite article having no flaws.

The contrast curves C illustrated in FIG. 4 denotes a flaw free area with no defects which is visually mapped and displayed in black, pixel by pixel in a flaw discrimination screen 40 as indicated in block 30 and illustrated in FIG. 9. The contrast curve C illustrated in FIG. 5 denotes an area of delamination. First and second porosity contrast curves C1 and C2 illustrated in FIG. 6 denote two different distinct layers of porosity with two different peaks P followed by two different shallow troughs ST. The contrast curve C illustrated in FIG. 7 denotes a distinct extended layer of porosity which is characterized by the contrast curve C including a characteristic leading peak LP, small or large, followed by the plateau PP.

Figure 8:
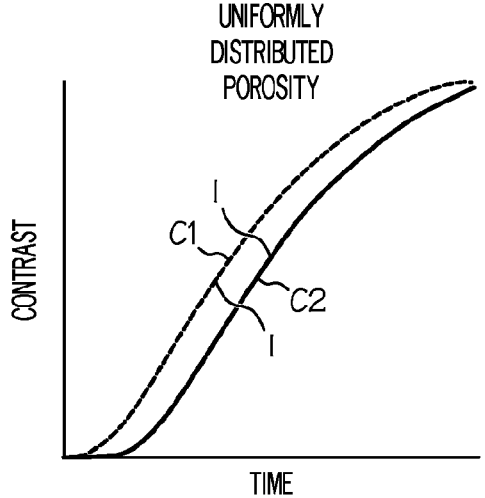
FIG. 8 is a graph of an exemplary contrast curve for a pixel in an area of the composite article having a uniformly distributed porosity flaw.

Illustrated in FIG. 8 is a no defect contrast curve C1 denoting an area of the object with no defects compared to a uniformly distributed porosity contrast curve C2 denoting an area of the object having uniformly distributed porosity. Both contrasts curves C1 and C2 are characterized by generally smooth curves with inflection points I over the characteristic time period TC. Pixels in areas of uniformly distributed porosity are characterized by the uniformly distributed porosity contrast curve C2 that is substantially shifted from the no defect contrast curve C1.

The contrast curve for each pixel is analyzed mathematically, empirically or semi-empirically to determine which flaw if any it represents. In the exemplary method illustrated herein, a color is assigned for each material characteristic type of flaw characterized by the analysis above. The pixels are mapped according to color coding in a visual display such as the one on a screen of the display monitor 17 in FIG. 1. For a given part or object the first one or few of the objects are analyzed in this manner to determine various types of contrast curves and their respective flaws and the characteristic time period TC. Then after this calibration step, production parts can be analyzed very quickly using the process and the visual display as described above.

Four views of the object 1, the composite gas turbine engine combustor liner in FIG. 1, are displayed in FIG. 9, each view representing a quadrant of the casing at 0, 90, 180, and 270 degrees around the casing. The color coding illustrated herein is gray for normal or areas designated as not having a flaw, white for areas of porosity, and black for areas of delamination. Also noted on the screen are the percentages of total area of the casing for each of the colors. The results of the analysis are thus available for an operator or inspector to use for NDE of the object. Other colors may be used to more clearly distinguish the flaws. One suggested color coding is yellow for layers of porosity, red for delaminations, and black for no flaws.

While there have been described herein what are considered to be preferred and exemplary embodiments of the present invention, other modifications of the invention shall be apparent to those skilled in the art from the teachings herein and, it is therefore, desired to be secured in the appended claims all such modifications as fall within the true spirit and scope of the invention. Accordingly, what is desired to be secured by Letters Patent of the United States is the invention as defined and differentiated in the following claims.

The invention claimed is:

1. A method for identifying material characteristic types of flaws in a composite object, the method comprising the steps of:
   a) rapidly heating the surface of the composite object;
   b) recording pixel intensities in a sequence of IR images, each image sequentially related to time elapsed since heating the surface in step (a);
   c) determining temperature-versus-time data for each of the pixels from the IR images; and
   d) determining what material characteristic type of flaw if any corresponds to each of the pixels using the temperature-versus-time data determined in step (c),
      step (d) including determining a contrast curve for each of the pixels from the temperature-versus-time data for each of the pixels and using the contrast curve in determining what type of flaws if any corresponds to each of the pixels, and the flaws including a layer of porosity characterized by a leading peak followed by a trough in the contrast curve.

2. A method for identifying material characteristic types of flaws in a composite object, the method comprising the steps of:
   a) rapidly heating the surface of the composite object;
   b) recording pixel intensities in a sequence of IR images, each image sequentially related to time elapsed since heating the surface in step (a);
   c) determining temperature-versus-time data for each of the pixels from the IR images; and
   d) determining what material characteristic type of flaw if any corresponds to each of the pixels using the temperature-versus-time data determined in step (c),
      step (d) including determining a contrast curve for each of the pixels from the temperature-versus-time data for each of the pixels and using the contrast curve in determining what type of flaws if any corresponds to each of the pixels, and the flaws including layers of porosity characterized by different leading peaks followed by different plateaus respectively in the contrast curves.

3. A method for identifying types of flaws in a composite object, the method comprising the steps of:
   a) rapidly heating the surface of the composite object;
   b) recording pixel intensities in a sequence of IR images, each image sequentially related to time elapsed since heating the surface in step (a);
   c) determining temperature-versus-time data for each of the pixels from the IR images; and
   d) determining what type of flaw if any corresponds to each of the pixels using the temperature-versus-time data determined in step (c);
   the contrast curve being a first contrast curve,
   determining a no defect second contrast curve calculated by;
   a1) rapidly heating no defect surface over a flaw free area of the object with no defects below the no defect surface;
   b1) recording pixel intensities in a sequence of IR images, each image sequentially related to time elapsed since heating the no defect surface in step (a1);
   c1) determining temperature-versus-time no defect data for each of the pixels from the IR images in step b1); and
   d1) determining a no defect second contrast curve for each of the pixels from the temperature-versus-time no defect data for each of the pixels determined in step (c1);
   the porosity being characterized by the first contrast curve being substantially shifted from the no defect second contrast reference curve and each of the porosity contrast curve and the no defect second contrast curve having an inflection point.

4. A method for identifying material characteristic types of flaws in a composite object, the method comprising the steps of:
   a) rapidly heating the surface of the composite object;
   b) recording pixel intensities in a sequence of IR images, each image sequentially related to time elapsed since heating the surface in step (a);
   c) determining temperature-versus-time data for each of the pixels from the IR images; and
   d) determining what material characteristic type of flaw if any corresponds to each of the pixels using the temperature-versus-time data determined in step (c),
      step (d) including determining a contrast curve for each of the pixels from the temperature-versus-time data for each of the pixels and using the contrast curve in determining what type of flaws if any corresponds to each of the pixels, and the step of determining the contrast curve calculating and storing synthetic thermal reference temperature-versus-time data and determining a synthetic reference curve from the stored synthetic thermal reference temperature-versus-time data and subtracting the synthetic reference curve from a temperature time curve determined from the temperature-versus-time data from step (c).

5. A method as claimed in claim 4, wherein the flaws including a delamination characterized by peaks in the contrast curve.

6. A method as claimed in claim 4, wherein the flaws including a layer of porosity characterized by leading peak followed by a trough in the contrast curve.

7. A method as claimed in claim 4, wherein the flaws including layers of porosity characterized by different leading peaks followed by different plateaus respectively in the contrast curves.

8. A method as claimed in claim 4, wherein the flaws including porosity characterized by a porosity contrast curve substantially shifted from a no defect contrast curve and each of the uniformly distributed porosity contrast curve and the no defect contrast curve having an inflection point.

9. A method for identifying material characteristic types of flaws in a composite object, the method comprising the steps of:
    a) rapidly heating the surface of the composite object;
    b) recording pixel intensities in a sequence of IR images, each image sequentially related to time elapsed since heating the surface in step (a);
    c) determining temperature-versus-time data for each of the pixels from the IR images; and
    d) determining what material characteristic type of flaw if any corresponds to each of the pixels using the temperature-versus-time data determined in step (c),
        step (d) including determining a contrast curve for each of the pixels from the temperature-versus-time data for each of the pixels and using the contrast curve in determining what type of flaws if any corresponds to each of the pixels,
        the flaws including delaminations characterized by the contrast curves having peaks,
        the flaws including distinct layers of porosity characterized by the contrast curves having leading peaks followed by troughs in the contrast curves,
        the flaws including distinct extended layers of porosity characterized by the contrast curves having leading peaks followed by plateaus in the contrast curves,
    the contrast curve being a contrast first curve,
    a no defect contrast second curve calculated by;
        a1) rapidly heating no defect surface over a flaw free area of the object with no defects below the no defect surface;
        b1) recording pixel intensities in a sequence of IR images, each image sequentially related to time elapsed since heating the no defect surface in step (a1);
        c1) determining temperature-versus-time no defect data for each of the pixels from the IR images in step b1); and
        d1) determining a second contrast second curve for each of the pixels from the temperature-versus-time no defect data for each of the pixels determined in step (c1); and
        the flaws including porosity characterized by the contrast first curve being substantially shifted from the no defect contrast second curve and each of the porosity contrast first curve and the no defect contrast second curve having an inflection point.

10. A method as claimed in claim 9, further comprising displaying areas of the object corresponding to the pixels characterized by the type of flaw and no flaw.

11. A method as claimed in claim 10, further comprising displaying the areas of the object in different colors corresponding to the pixels characterized by the types of flaws and no flaws.

12. A method as claimed in claim 9, further comprising determining the contrast curve by determining a synthetic reference curve from previously calculated and stored synthetic thermal reference temperature-versus-time data and subtracting the synthetic reference curve from a temperature time curve determined from the temperature-versus-time data from step (c).

13. A method as claimed in claim 12, further comprising displaying areas of the object corresponding to the type of flaw and no flaw characterized by the contrast curves of the pixels.

14. A method as claimed in claim 13, further comprising displaying the areas of the object in different colors corresponding to the types of flaws and no flaws characterized by the contrast curves of the pixels.

* * * * *